(12) United States Patent
Bisse

(10) Patent No.: US 10,969,396 B2
(45) Date of Patent: Apr. 6, 2021

(54) IN VITRO METHOD, USE OF AN AGENT AND COLLECTION DEVICE FOR THE INHIBITION OF COAGULATION IN BLOOD

(71) Applicant: Petra Weser-Bisse, Denzlingen (DE)

(72) Inventor: Emmanuel Bisse, Denzlingen (DE)

(73) Assignee: Petra Weser-Bisse, Denzlingen (DE)

( * ) Notice: Subject to any disclaimer, the term of this patent is extended or adjusted under 35 U.S.C. 154(b) by 242 days.

(21) Appl. No.: 14/770,576

(22) PCT Filed: Feb. 26, 2014

(86) PCT No.: PCT/EP2014/053691
§ 371 (c)(1),
(2) Date: Aug. 26, 2015

(87) PCT Pub. No.: WO2014/131784
PCT Pub. Date: Sep. 4, 2014

(65) Prior Publication Data
US 2016/0003853 A1    Jan. 7, 2016

(30) Foreign Application Priority Data
Feb. 28, 2013 (EP) ..................... 13157271

(51) Int. Cl.
*G01N 33/86* (2006.01)
*A61B 5/15* (2006.01)
*A61B 5/153* (2006.01)

(52) U.S. Cl.
CPC ......... *G01N 33/86* (2013.01); *A61B 5/15003* (2013.01); *A61B 5/153* (2013.01); *A61B 5/150343* (2013.01); *A61B 5/150755* (2013.01); *A61B 5/150992* (2013.01)

(58) Field of Classification Search
CPC ................ G01N 33/86; A61B 5/15003; A61B 5/150755
See application file for complete search history.

(56) References Cited

U.S. PATENT DOCUMENTS

| | | | |
|---|---|---|---|
| 6,716,392 B1 | 4/2004 | Putcha et al. | |
| 6,913,932 B2* | 7/2005 | Maples | A01N 1/02 252/408.1 |
| 2002/0153316 A1* | 10/2002 | Nanba | B01D 53/228 210/650 |
| 2004/0137417 A1* | 7/2004 | Ryan | B01L 3/5082 435/2 |
| 2006/0210429 A1* | 9/2006 | Hunsley | B01L 3/5082 422/550 |

FOREIGN PATENT DOCUMENTS

| | | |
|---|---|---|
| EP | 1884778 A1 | 2/2008 |
| EP | 1950567 A1 | 7/2008 |
| JP | S62242854 A | 10/1987 |

OTHER PUBLICATIONS

Lee et al., Anticoagulation Techniques in Aphresis: From Heparin to Citrate and beyond, Journal of Clinical Aphresis, 2012, vol. 3, p. 117-125.*
https://pubchem.ncbi.nlm.nuh.gov/compound/citric_acid#section=Viscosity.*
Machine translation of JP62242854 (Year: 1987).*
Baca et al. EDTA is a better anticoagulant than heparin or citrate for delayed blood processing for plasma DNA analysis., Clinical Chemistry, vol. 50, p. 256-257. (Year: 2004).*
PCT International Search Report issued on corresponding PCT International Application No. PCT/EP2014/053691 filed Feb. 26, 2014.

* cited by examiner

*Primary Examiner* — Taeyoon Kim
*Assistant Examiner* — Tiffany M Gough
(74) *Attorney, Agent, or Firm* — Locke Lord LLP; Nicholas J. DiCeglie, Jr.

(57) ABSTRACT

The present invention relates to a method and a use of an agent for the in vitro inhibition of coagulation in blood and a blood collection device provided for said method and use.

3 Claims, 2 Drawing Sheets

Figure 1:
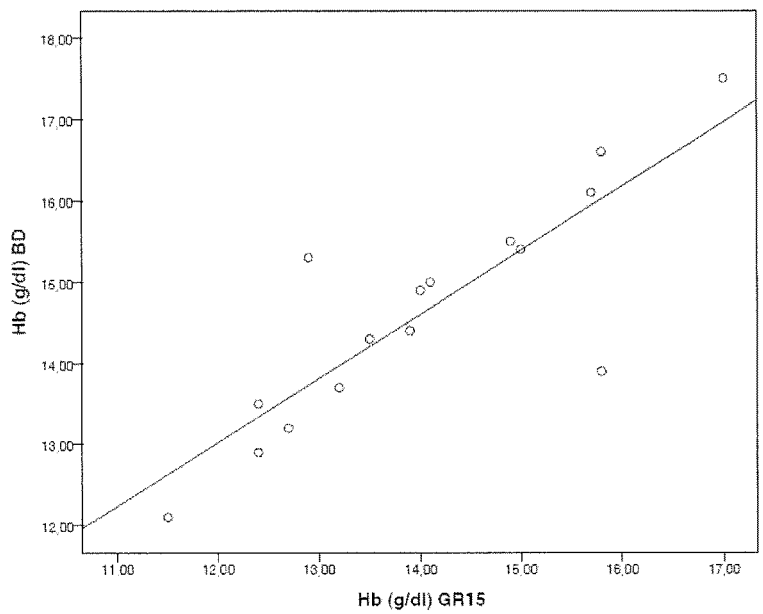
Figure 1:
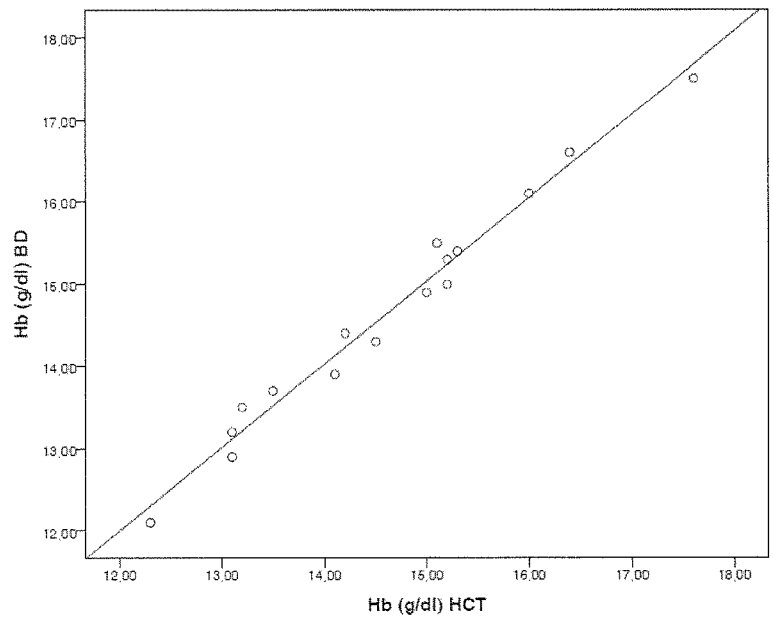

Results of Example 29A y= 0.789x+3.555, $R^2$=0.72

Results of Example 29B y=1.013x-0.156, $R^2$=0.98

Results of Example 30A y=0.499x+ 63.15, $R^2$=0.448

Results of Example 30B y=0.874x+13.318 , $R^2$=0.955

IN VITRO METHOD, USE OF AN AGENT AND COLLECTION DEVICE FOR THE INHIBITION OF COAGULATION IN BLOOD

CROSS-REFERENCE TO RELATED APPLICATIONS

This application is a national stage application filed under 35 U.S.C. § 371 of International Application PCT/EP2014/053691 (published Sep. 4, 2014 as WO 2014/131784) having an International filing date of Feb. 26, 2014 and which claims priority to European Patent Application No. EP 13157271.1, filed Feb. 28, 2013, the entire contents each of which are incorporated herein in their entireties.

BACKGROUND OF THE INVENTION

Blood sampling and testing are routinely carried out for various diagnostic purposes. The accurate and precise determination of blood constituents or parameters is oftentimes required to be able to draw valid and reliable diagnostic and prognostic conclusions. In this respect results from diagnostic tests of blood can be strongly affected by preanalytical circumstances and conditions. In many cases it is desirable to maintain blood after withdrawal in a substantially physiologically native state. Depending on the particular situation and the type(s) of (extra)cellular component(s) and constituent(s) to be determined, it may be necessary to use whole blood, or also preferable to use plasma samples instead of serum.

Coagulation and platelet aggregation in blood leading to clotting can occur when blood is withdrawn by puncturing blood vessels and when it is collected in and comes in contact with sample containers due to the activation of platelets and coagulation factors. Further, this process can result in for example lysis of cells and changes of cellular and extracellular concentrations of blood constituents. Moreover, subsequent in vitro coagulation tests and blood count are precluded. In order to prepare and provide whole blood and plasma samples for in vitro diagnostic investigations additives which inhibit blood and/or plasma from coagulation and clotting and which are generally called anticoagulants are commonly added to and mixed with blood immediately after sample collection. More specifically, the term anticoagulant refers to inhibitors of plasmatic blood clotting or coagulation, distinguishable from inhibitors of platelet aggregation. Both calcium ions and thrombin are required for the clotting process. Therefore, salts of ethylenediaminetetraacetic acid (EDTA salts) or citrate salts which can chelate calcium ions, and heparin salts which can inhibit thrombin activity are typically used as anticoagulants. For a general description of the processes and components involved in coagulation and primary and secondary hemostasis, comprising the coagulation cascade and the intrinsic and extrinsic pathway, it is referred to "Textbook of Biochemistry with Clinical Correlations", 5th edition, T. M. Devlin (ed.), Wiley, 2002.

In particular, sodium, lithium or ammonium salt of heparin, $K_2EDTA$, $K_3EDTA$, $Na_2EDTA$ and trisodium citrate are commonly used as anticoagulants in diagnostic laboratory investigations (see e.g. WHO document "Use of Anticoagulants in Diagnostic Laboratory Investigations" (WHO/DIL/LAB/99.1 Rev. 2, 2002)). Buffering and adjustment of pH, for example in the physiological range, may optionally be performed, for example for citrate by adding citric acid. Moreover, stabilizing agents may be comprised besides the anticoagulant. The above-mentioned anticoagulants are used to obtain whole blood samples for hematologic analyses (e.g. full blood cell counts and white blood cell differential analysis) or to obtain plasma samples for hemostasis and clinical chemistry analyses.

However, for diagnostic applications these typically used anticoagulants have certain drawbacks and shortcomings due to the interference with certain analytical methods and the changing of the concentration of certain constituents to be measured. For example, sample contamination with clinically relevant cations such as $Na^+$, $Li^+$, $K^+$ and $NH_4^+$ from these anticoagulants, which are added in comparatively high concentrations, can be problematic in view of determination of these ions as well as hyperosmolarity/change in osmolarity. The latter can lead to water outflow from cells, loss of cellular integrity, ion leakage and thus also to interference in subsequent analyte testing. Likewise chelation of e.g. $Ca^{2+}$, $Mg^{2+}$ or $Zn^{2+}$ can interfere with the analysis of these cations, and enzymes—also in subsequent assays—whose structure/function depend on these ions can also be affected, especially when the divalent cations are strongly depleted by a high concentration of chelating anticoagulant. The polyanionic heparin may inhibit metabolic or catalytic reactions. Moreover, the determination of several laboratory parameters by hematologic tests, coagulation tests as well as clinical chemistry analyses from a single sample is precluded. The need to provide several samples with different anticoagulants or different concentrations of anticoagulant entails extra time, cost and potential for errors in the preanalytical and analytical procedures.

There is a need in the art to simplify the inhibition of coagulation in blood during preanalytics and to make it more robust and economical while enabling the subsequent testing of blood constituents and providing benefits in terms of sample handling, storage, transport and throughput and, as far as possible, accuracy, without however affecting anticoagulation efficacy.

SUMMARY OF THE INVENTION

The object is solved by the in vitro method of the invention, the use of a blood collection device of the invention, the use of an agent of the invention, the blood collection device of the invention and the kit of the invention, while preferred embodiments are set forth as further described below.

The present invention in particular provides the following items including main aspects and preferred embodiments, which respectively alone and in combination particularly contribute to solving the above object and eventually provide additional advantages.

In one aspect, the invention provides an in vitro method for the inhibition of coagulation in blood, wherein blood is mixed after its withdrawal with an agent comprising as the only anticoagulant a substance provided as free acid having a $pK_a$ of $\geq 0.9$.

In one embodiment of the method of the invention, the substance provided as free acid having a $pK_a$ of $\geq 0.9$ denotes a substance provided as free carboxylic acid having a $pK_a$ of $\geq 0.9$.

In another embodiment of the method of the invention, said substance provided as free acid having a $pK_a$ of $\geq 0.9$ comprises at least two carboxyl groups per molecule, preferably comprises at least three carboxyl groups per molecule.

In still another emnodiment of the method of the invention, said agent consists of (i) said substance provided as free acid having a $pK_a$ of ≥0.9; or (ii) said substance provided as free acid having a $pK_a$ of ≥0.9 dissolved in a solvent.

Optionally, no any further substance than the specified agent is mixed with the withdrawn blood.

In another embodiment of the method of the invention, wherein subsequently at least one test is carried out for the determination of at least one blood component, preferably at least two tests are carried out for the determination of at least two blood components.

In yet another embodiment of the method of the invention, the concentration of said substance provided as free acid having a $pK_a$ of ≥0.9 is at least 0.1 mmol/L of blood to be mixed with, preferably is in the range from 0.1 to 100 mmol/L of blood to be mixed with, more preferably in the range from 1 to 50 mmol/L of blood to be mixed with, even more preferably in the range from 2 to 32 mmol/L of blood to be mixed with, and most preferably in the range from 2 to 10 mmol/L of blood to be mixed with.

In still another embodiment of the method of the invention, the lysis of blood cells is essentially avoided.

In another embodiment of the method of the invention, said substance provided as free acid having a $pK_a$ of ≥0.9 is provided as a powder or in lyophilized form.

In certain embodiments of the method of the invention, in case (ii) the solvent is selected from the group consisting of an aqueous solution, water, and alcohol and mixtures of water and alcohol, preferably is water or ethanol, and more preferably is water.

In another embodiment of the method of the invention, the withdrawn blood is whole blood.

In certain embodiments of the method of the invention, the amount of at least one blood component is determined, preferably the amounts of at least two blood components are determined, by comprising the following steps:

(a) providing a blood collection device containing, placed in the device, the agent of the invention, optionally further containing a pH modifying agent and/or an ammonium salt $NR_4X$, wherein each R independently is hydrogen, linear $C_1$-$C_6$ alkyl, branched $C_3$-$C_6$ alkyl, unsubstituted phenyl or substituted phenyl, and X is halide and preferably is chloride;

(b) placing blood in the blood collection device;

(c) mixing said agent with blood in the blood collection device;

optionally (d) storing the blood in the blood collection device for a desired period of time; and (e) determining the amount of the at least one blood component, preferably of the at least two blood components, in the blood sample.

In another embodiment of the method of the invention, wherein steps (b) to (d) are carried out at a temperature from 0 to 37° C., and wherein steps (b) and (c) are preferably carried out at room temperature.

In still another embodiment of the method of the invention, instead of steps (a) and (b), a step is carried out which comprises placing blood in a blood collection device and subsequently placing the agent in the blood collection device.

In yet another embodiment of the method of the invention, the blood in step (b) is whole blood.

In certain embodiments of the method of the invention, in step (e) the determination of the amount of the at least one blood component is carried out using conventional physical, chemical, enzymatic and/or immunological methods, including combinations thereof.

In another embodiment of the method of the invention, said substance provided as free acid having a $pK_a$ of ≥0.9 is selected from the group consisting of citric acid, tricarballylic acid, ethylenediaminetetraacetic acid, diethylenetriaminepentaacetic acid, benzenepentacarboxylic acid, mellitic acid, and tetrahydrofuran-2,3,4,5-tetracarboxylic acid or mixtures thereof, preferably is citric acid, tricarballylic acid or ethylenediaminetetraacetic acid, and more preferably is citric acid. In particular embodiments of the invention, citric acid is anhydrous citric acid and/or citric acid monohydrate, preferably is citric acid monohydrate.

In still another embodiment of the method of the invention, in step (a) the concentration of said substance provided as free acid having a $pK_a$ of ≥0.9 is at least 0.1 mmol/L of blood to be mixed with, preferably is in the range from 0.1 to 100 mmol/L of blood to be mixed with, more preferably in the range from 1 to 50 mmol/L of blood to be mixed with, even more preferably in the range from 2 to 32 mmol/L of blood to be mixed with, and most preferably in the range from 2 to 10 mmol/L of blood to be mixed with.

In another aspect, the present invention provides for the use of a blood collection device for collecting and optionally storing blood in vitro, wherein in the device blood i s mixed after its withdrawal with an agent of the invention, and wherein coagulation in blood is thereby inhibited. In certain embodiments, wherein blood collected in a single device and mixed with said agent is subsequently subjected to at least one test for the determination of at least one blood component, preferably to multiple tests comprising at least one hematologic test, at least one coagulation test and at least one further clinical chemistry analysis.

In another aspect, the invention provides for the use of an agent comprising as the only anticoagulant a substance provided as free acid having a $pK_a$ of ≥0.9 for effecting inhibition of coagulation of blood in vitro. In certain embodiments, the agent is an agent of the invention.

In still another aspect, the invention provides a blood collection device, wherein an agent of the invention is provided in the device, and wherein the substance provided as free acid having a $pK_a$ of ≥0.9 is the only provided anticoagulant to be mixed with blood. In certain embodiments, the blood collection device comprises a device which is capable of being connected with a conventional blood withdrawal device.

In another aspect, the invention provides a kit comprising:
the blood collection device according to the invention, and
test substance(s) for the determination of at least one blood component in collected blood.

DETAILED DESCRIPTION OF THE INVENTION

In the following, the present invention is described in more detail while referring to preferred embodiments and examples, which are presented however for illustrative purposes and shall not be construed to limit the invention in any way.

A first aspect of the present invention is an in vitro method for the inhibition of coagulation in blood, wherein blood is mixed after its withdrawal with an agent comprising as the only anticoagulant a substance provided as free acid having a $pK_a$ of ≥0.9.

The logarithmic constant $pK_a$ is equal to $-\log_{10}K_a$, wherein $K_a$ is the acid dissociation constant. For polyprotic acids $pK_a$ here denotes the logarithmic constant for dissociation of the first proton, i.e. $pK_{a1}$. Preferably the substance provided as free acid has a p$K_a$ of ≥1.4, more preferably has a p$K_a$ of ≥2, even more preferably has a p$K_a$ of ≥2.5 and most preferably has a p$K_a$ of ≥3.

It was surprisingly found that coagulation in blood could be effectively inhibited in vitro when blood was mixed with a free acid substance having a p$K_a$ of ≥0.9, with the mixing preferably occurring simultaneously with or immediately or expeditiously after sample collection, wherein the sample preferably is withdrawn or collected whole blood. In particular, according to the present invention an efficient method is provided when free acid having a p$K_a$ of ≥0.9 is provided as the only anticoagulant, i.e. the only substance provided for the purpose of and effective in inhibiting coagulation. In a preferred embodiment the free acid substance having a p$K_a$ of ≥0.9 is a free carboxylic acid substance having a p$K_a$ of ≥0.9.

Optionally, use of any substance other than the specified anticoagulant agent to be mixed with the withdrawn blood can be omitted. A substance provided as free acid having a p$K_a$ of ≥0.9 according to the invention preferably is an organic Brønsted acid having a p$K_a$ of ≥0.9. In an embodiment the substance provided as free acid having a p$K_a$ of ≥0.9 is an organic Brønsted acid comprising at least one carboxyl group per molecule, preferably at least two carboxyl groups per molecule, more preferably at least three carboxyl groups per molecule, wherein in the acid as provided (all of) the carboxyl group(s) in the molecule is (are) protonated, that is to say the carboxyl group(s) is (are) not dissociated. It is understood that in the substance provided as free acid having a p$K_a$ of ≥0.9 conjugate base may only be present as minor impurity. Accordingly in an embodiment where said substance is provided as free carboxylic acid carboxylate groups may only be present as minor impurity, preferably the substance is substantially free of carboxylate, more preferably the substance is free of carboxylate. Besides such possible impurity, according to the present invention a carboxylate salt, let alone the salt of the respectively given carboxylic acid, shall not be used as anticoagulant and is preferably entirely excluded from the agent, and especially salts of EDTA and citrate are excluded. Furthermore, heparin salt is not provided as anticoagulant nor is it comprised in the agent. Considering that conventionally salts of EDTA and citrate as well as heparin salts are used as anticoagulant, it is unexpected that a substance provided as free acid having a p$K_a$ of ≥0.9, preferably a substance provided as free carboxylic acid having a p$K_a$ of ≥0.9, when so mixed in vitro with blood after its withdrawal, exhibits an inhibitory effect against coagulation. Inhibition of coagulation according to the present invention means that, instead of coagulating, blood after its withdrawal and careful mixing with the inventive agent remains fluid. Furthermore, late or delayed clotting can be advantageously avoided. Preferably, inhibition of coagulation according to the present invention means that in a conventional automated analysis system a clot-detection-system detects same or fewer positive events, i.e. clots, compared to conventional anticoagulation sampling. More preferably, in a conventional automated analysis system a clot-detection-system detects considerably fewer events, i.e. clots, compared to conventional anticoagulation sampling.

Without wishing to be bound by theory, it is thought that in the blood the acidic protons from the provided free acid having a p$K_a$ of ≥0.9 specifically and/or non-specifically (e.g. through electrostatics, hydrogen bonding, acid-base reaction and proton transfer, etc.), but in a manner at least in part distinct from other cations, interact with blood components, such as proteins (e.g. enzymes) and membrane constituents (e.g. phospholipids), and reversibly or irreversibly interfere with the proper biomolecular structure and function of said blood components. Considering the specific size and the charge, the protons may suitably interact with proteins to effect particular structural and physicochemical changes and thus specifically affect protein function, for example of serine proteases and also in terms of interactions between protein complexes. When free carboxylic acid is preferably used furthermore the protons and the anionic carboxylates formed in the blood may interfere with the $Ca^{2+}$-dependent association of coagulation factors and phospholipids. Overall an inhibitory effect on the enzymatic coagulation cascade is observed. The term anticoagulant as used herein thus preferably denotes inhibitors of plasmatic blood clotting or coagulation. In the present invention complex formation via chelation of $Ca^{2+}$ with the anticoagulant is believed to play, if at all, at most only a minor role. It has been found that when free carboxylic acid having a p$K_a$ of ≥0.9 is used as the only anticoagulant the measured free $Ca^{2+}$ plasma concentration can be similar to and slightly higher than in the corresponding serum, while $Ca^{2+}$ is almost completely depleted in plasma with salts of EDTA and citrate (see also Example 18).

In one embodiment of the method the agent consists of the substance provided as free acid having a p$K_a$ of ≥0.9, or the substance provided as free acid having a p$K_a$ of ≥0.9 dissolved in a solvent. In a preferred embodiment of the method the agent consists of a substance provided as free carboxylic acid having a p$K_a$ of ≥0.9, or a substance provided as free carboxylic acid having a p$K_a$ of ≥0.9 dissolved in a solvent. It is preferred that the agent contains the free acid having a p$K_a$ of ≥0.9, preferably the free carboxylic acid, as the only acid. Preferably the solvent is selected from the group consisting of an aqueous solution, water, and alcohol and mixtures of water and alcohol, more preferably is water or ethanol, and even more preferably is water. Additional additive commonly used for preserving blood, wherein said additional additive is not an anticoagulant and does not comprise acid, may optionally be comprised, for example an antiglycolytic agent.

According to an aspect of the invention preferably at least one test is carried out for the determination of at least one blood component subsequent to mixing blood with the agent according to the present invention. More preferably, at least two tests are carried out for the determination of at least two blood components subsequent to mixing blood with the agent according to the present invention. Advantageously the present invention allows the determination of several laboratory parameters by hematologic tests, coagulation tests and/or clinical chemistry analyses from a single sample. This way the present method provides for effective anticoagulation while making the blood amenable to downstream diagnostic analyses in a generally applicable and broadly useful manner, in particular diagnostic analysis suitable to assess pathological and/or therapeutic implications. The determination of the amount of the at least one blood component is preferably carried out using conventional physical, chemical, enzymatic and/or immunological methods, including combinations thereof. In a preferred embodiment, besides minor impurity, substantially no cations, preferably no cations other than protons from the free acid having a p$K_a$ of ≥0.9, preferably the free carboxylic acid having a p$K_a$ of ≥0.9, are added to the blood. Therefore, in this case contamination with and interference from other cations, including clinically relevant cations, is favourably avoided. Moreover, in said preferred embodiment, besides minor impurity, there are substantially no inorganic anions, preferably no inorganic anions of mineral acid provided. Furthermore, hyperosmolarity and the lysis of blood cells are preferably essentially avoided, more preferably are avoided. Therefore, the determination of a multitude of laboratory parameters by hematologic, coagulation as well as clinical chemistry analyses from a single sample becomes advantageously possible, avoiding the detrimental effects of interfering ions.

Changes in the intracellular and extracellular ion concentrations can generally lead to hyperosmolarity and hemolysis. In principle when free acid is used as anticoagulant a disturbance in the electrochemical balance between the inside and outside of cells may, for example, results in a change of the plasmatic chloride concentration, or the concentration of uric acid. In the case of free carboxylic acid the extent of such a possible change depends on the number of carboxyl groups. Without wishing to be bound by theory, this may be caused by an increase of hydrogen ions in the extracellular fluid of the blood along with the presence of carboxylate ions generated. In particular, hydrogen ions may react with extracellular bicarbonate anions and the flow of ions from the outside to the inside of the cells, and vice versa, may be affected, resulting for example in a chloride ion shift. Considering that carboxylate ions barely penetrate, if at all, into the red blood cells, chloride ions may be kept in the cells functioning as counterions for intracellular cations. In such situations hemolysis of the red blood cells may be induced, which in turn could negatively influence the determination of not only chloride ions but also of haemoglobin. Furthermore, changes in osmolarity and the outflow of water from the blood cells could lead to a possible dilution effect and possible impairment of cellular integrity due to the desiccation of blood cells.

In the present invention, optionally furthermore an ammonium salt $NR_4X$ and/or a pH modifying agent may be provided together with the anticoagulant, preferably concomitantly but alternatively also slightly time-displaced. This can provide significant further benefits in terms of stabilization and preservation of a blood sample and of further facilitating the reliable determination of blood components.

It was surprisingly found that a possible impairment of cellular integrity and even lysis of blood cells could be favourably inhibited by additionally adding an ammonium salt $NR_4X$, wherein each R independently is hydrogen, linear $C_1$-$C_6$ alkyl, branched $C_3$-$C_6$ alkyl, unsubstituted phenyl or substituted phenyl, and X is preferably halide and more preferably is chloride. Tetramethylammonium chloride and/or tetraethylammonium chloride are even more preferred, and tetramethylammonium chloride is particularly preferred. Preferably, when ammonium salt $NR_4X$ is added, the concentration of the ammonium salt $NR_4X$ is 0.01 to 100 µmol/mL blood, preferably is 5 to 25 µmol/mL blood, and more preferably is 15 to 20 µmol/mL blood. Tetramethylammonium chloride in a concentration of 15 to 20 µmol/mL blood is particularly preferred.

Moreover, it was surprisingly found that a possible impairment of cellular integrity and even lysis of blood cells could also be favourably inhibited by adding a pH modifying agent. Said pH modifying agent favourably does not interfere with the laboratory parameters to be tested. As pH modifying agent organic amine is preferably used, more preferably triethanolamine, ethanolamine and/or 2-amino-2-methylpropanol are used. For example, when a pH modifying agent is added and free acid is provided in solution, preferably a pH value between 2.2 and 3.0 is set. Inorganic bases such as sodium hydroxide are suitably avoided.

Figure 2:
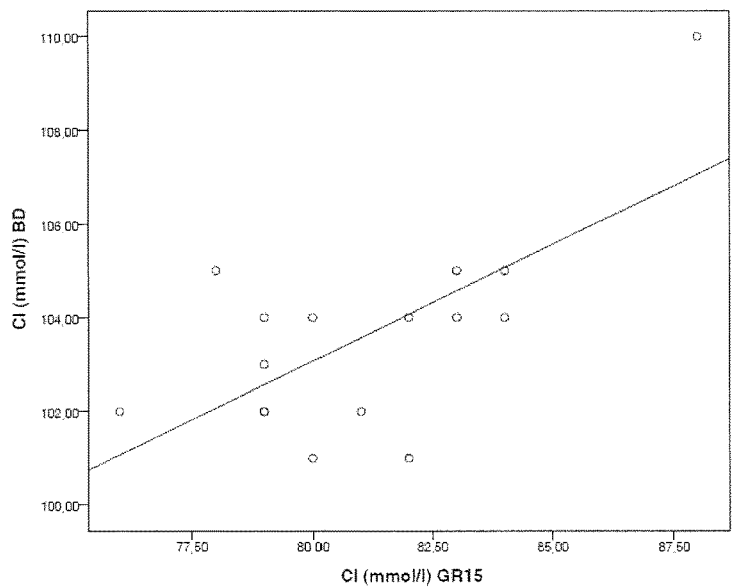
Figure 2:
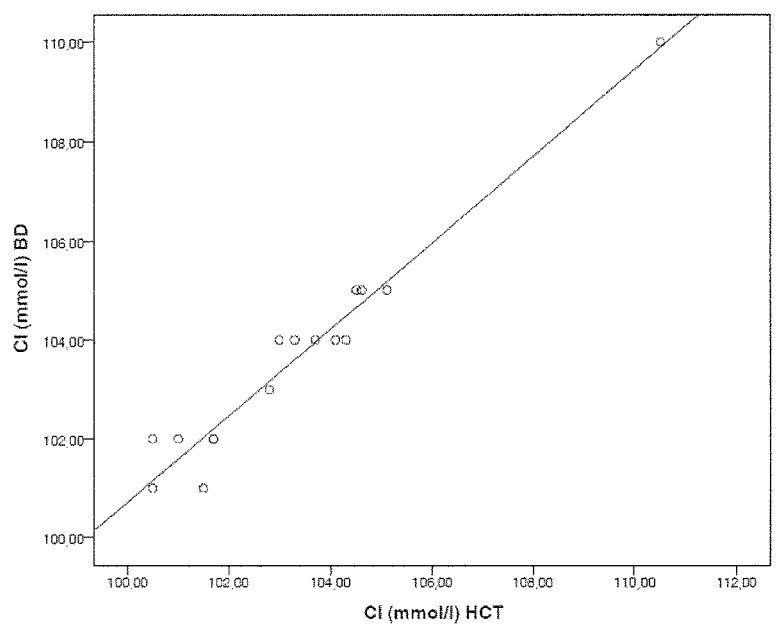

It was particularly found that surprisingly a possible impairment of cellular integrity and even lysis of blood cells could be especially favourably inhibited by adding a combination of the ammonium salt $NR_4X$ and the pH modifying agent. This way the correct determination of both haemoglobin and chloride ions is even more surely possible (see Examples 29 and 30 and FIGS. 1 and 2). This is also an indication for a still more favourable condition in the electrochemical balance between the inside and the outside of the cells. This way hemolysis can be inhibited particularly efficiently and effectively. This advantageous effect is especially relevant in cases where occurrence of hemolysis must be significantly reduced or even safely and surely avoided. Hemolysis can for example destabilize a sample and prevent prolonged storage. Furthermore, hemolysis can be detrimental to blood testing and diagnostics because, for example, mixing of plasma components with cellular components from the lysed cells can lead to spurious results for both plasma and cell analyses or even prevent such analyses altogether. Therefore, inhibiting hemolysis is advantageous for the reliable determination of blood components. This further improved stabilization and preservation of a blood sample can provide longer storage and a more reliable determination of blood components and thus improved diagnostics.

The concentration of the substance provided as free acid having a $pK_a$ of ≥0.9, preferably the substance provided as free carboxylic acid having a $pK_a$ of ≥0.9, is preferably at least 0.1 mmol/L of blood to be mixed with, more preferably is in the range from 0.1 to 100 mmol/L of blood to be mixed with, even more preferably in the range from 1 to 50 mmol/L of blood to be mixed with, yet even more preferably in the range from 2 to 32 mmol/L of blood to be mixed with, and most preferably in the range from 2 to 10 mmol/L of blood to be mixed with. In an embodiment the concentration of the substance provided as free acid having a $pK_a$ of ≥0.9 is set such that after mixing of said substance with blood the blood sample exhibits a pH in the range from 6.0 to 7.4. According to an embodiment of the present invention the amount of the substance provided as free acid having a pKa of ≥0.9 is set such that if dissolved in a desired amount of water the obtained aqueous solution exhibits a pH of ≥1.5. In a preferred embodiment the amount of the substance provided as free acid having a pKa of ≥0.9 is set such that if dissolved in a desired amount of water the obtained aqueous solution exhibits a pH of ≥1.5 and that when mixed with blood the blood sample exhibits a pH in the range from 6.0 to 7.4. In a preferred embodiment the free acid is provided such that its concentration is adjusted to below 20 mmol/L of blood to be mixed with, preferably below 15 mmol/L of blood to be mixed with. Particularly preferred is a concentration in the range from 2 to 10 mmol/L of blood to be mixed with. This allows to suitably adjust the pH value in the blood sample.

Preferably the substance provided as free acid having a pKa of ≥0.9, more preferably the substance provided as free carboxylic acid, is selected from the group consisting of citric acid, tricarballylic acid, ethylenediaminetetraacetic acid, diethylenetriaminepentaacetic acid, benzenepentacarboxylic acid, mellitic acid, and tetrahydrofuran-2,3,4,5-tetracarboxylic acid or mixtures thereof, more preferably is citric acid, tricarballylic acid or ethylenediaminetetraacetic acid, and even more preferably is citric acid. In an embodiment citric acid is anhydrous citric acid and/or citric acid monohydrate, and citric acid monohydrate is most preferred. According to the invention the substance provided as free acid having a $pK_a$ of ≥0.9 is preferably provided as a powder or in lyophilized form.

In an embodiment according to the above aspect of the invention the amount of at least one blood component is determined by comprising the following steps: a blood collection device is provided which contains, placed in the device, the agent according to the invention, and optionally further contains an ammonium salt $NR_4X$ and/or a pH modifying agent; blood, preferably whole blood, is placed in said blood collection device; said agent is mixed with blood in the blood collection device; optionally the blood is stored in the blood collection device for a desired period of time, for example until assigned tests are carried out; and the amount of the at least one blood component in the blood sample is determined. Preferably, placing of the blood in the blood collection device, mixing and the optional storage are carried out at a temperature from 0 to 37° C., and placing of the blood in the blood collection device and mixing more preferably are carried out at room temperature. Instead of providing a blood collection device containing the agent according to the invention and placing blood in said blood collection device, alternatively a step may be carried out which comprises placing blood in a blood collection device and subsequently placing the agent in the blood collection device. Optionally, an ammonium salt $NR_4X$ and/or a pH modifying agent may be added. In a preferred embodiment the amounts of at least two blood components are determined.

Another aspect of the invention is the use of a blood collection device for collecting and optionally storing blood in vitro, wherein in the device blood is mixed after its withdrawal with the agent according to the present invention, and wherein coagulation in blood is thereby inhibited. Unexpectedly it was found in the present invention that an efficient inhibitory effect against coagulation and clotting is obtained when blood is mixed in the device with the agent which comprises as the only anticoagulant a substance provided as free acid having a $pK_a$ of $\geq 0.9$. In an embodiment blood is collected in a single device and mixed with the agent according to the invention and is subsequently subjected to at least one test for the determination of at least one blood component, preferably to multiple tests comprising at least one hematologic test, at least one coagulation test and at least one further clinical chemistry analysis. According to this aspect of the invention the number of collection tubes required for the different fields of laboratory medicine can be considerably reduced, which in turn allows to optimize and render more efficient laboratory activity and workflow and to reduce sample volume and turnaround time. Furthermore, the use of only a single effective anticoagulant for the different fields in clinical laboratories, i.e. hematology, clinical chemistry and hemostaseology, can expedite the process in emergency situations. The use of a single sample from a single blood collection tube is however not only very useful in emergency situations but also for pediatric patients and for patients from whom it is difficult to obtain more than one blood sample. Moreover, further biochemical analyses that were not initially anticipated or requested for the initial examination may advantageously be carried out on account of the broad test compatibility of the anticoagulant according to the invention (see also Examples 1-28). The broad applicability for ex vivo diagnostic analytics is beneficial to patient care and convenience.

In another aspect the invention relates to the use of an agent comprising as the only anticoagulant a substance provided as free acid having a $pK_a$ of $\geq 0.9$ for effecting inhibition of coagulation of blood in vitro.

Another aspect of the invention is a blood collection device, wherein the agent according to the present invention is provided in the device, and wherein the substance provided as free acid having a $pK_a$ of $\geq 0.9$ is the only provided anticoagulant to be mixed with blood. Preferably a device is comprised which is capable of being connected with a conventional blood withdrawal device. Conventional blood collection tubes including evacuated blood collection tubes such as vacutainer and aspiration systems such as monovette are known in the art. Besides the above-mentioned advantages in terms of use, the present invention can provide further economic advantages with respect to the manufacture of blood collection tubes as well as stocking logistics of collections tubes at the manufacturers and clinical laboratories.

Another aspect of the invention relates to a kit which comprises the blood collection device of the present invention and test substance(s) for the determination of at least one blood component in collected blood.

The following examples are merely illustrative of the present invention and they should not be considered as limiting the scope of the invention in any way. The examples and modifications or other equivalents thereof will become apparent to those skilled in the art in the light of the present entire disclosure.

Examples and Comparative Examples

Materials Used and Method
Materials

Citric acid monohydrate (CA), tricarballylic acid (TCA), ethylenediaminetetraacetic acid (EDTA), diethylenetriaminepentaacetic acid (DTPA), mellitic acid (MELA), and benzenepentacarboxylic acid (BPCA) were from Sigma-Aldrich, Germany. Tetrahydrofuran-2,3,4,5-tetracarboxylic acid (THTCA) was from TCI, Germany. Pristine blood collection tubes, i.e. tubes as originally provided not containing or respectively not filled or coated with additive, were from KABE Labortechnik GmbH, Germany, denoted KABEVETTE (GR). In said provided pristine tubes were respectively placed: 5.4 mmol of CA per L of blood to be mixed with, 31.2 mmol of TCA per L of blood to be mixed with, 2.3 mmol of EDTA per L of blood to be mixed with, 2.2 mmol of DTPA per L of blood to be mixed with, 3.1 mmol of MELA per L of blood to be mixed with, 4.6 mmol of THTCA per L of blood to be mixed with, and 8.0 mmol of BPCA per L of blood to be mixed with. For comparison, blood collection tubes with tripotassium EDTA ($K_3$EDTA), Serum Separator tubes with clot activator (SST), and 3.2% sodium citrate tubes were used which were from Becton Dickinson (BD).

Blood Collection and Sampling Protocol

Blood was collected from the antecubital vein from volunteers who had previously given their informed consent. For each subject, freshly drawn blood was collected into the corresponding tubes such that respectively a blood sample according to the present invention, a serum sample (SST (BD)), a citrate blood sample (citrate(BD)), and a potassium EDTA blood sample ($K_3$EDTA(BD)) were obtained. Tubes were filled with blood completely to the mark (4.9 mL), and for tubes containing anticoagulant the blood was mixed well with the respective anticoagulant by inverting the tubes 4 times immediately after blood collection. Serum samples were treated according to the protocol of the manufacturer and used for biochemical analysis. Whole blood potassium EDTA ($K_3$EDTA(BD)) and inventive samples were used first for hematologic determinations and were then centrifuged. The inventive and citrate plasma samples (citrate (BD)) were used for both haemostasis and biochemical determinations. Potassium EDTA plasma was also used for biochemical determinations.

It was found that coagulation was effectively inhibited in the tubes according to the present invention. Subsequently a multitude of laboratory parameters in a sample from respectively a single blood collection device according to the present invention could be determined and evaluated, and depending on the particular test, be compared to either of $K_3$EDTA(BD), citrate(BD) or SST (BD) samples. In Examples 1-27 results using CA (denoted GR 15) are shown. Example 28 shows results for various free acids having a $pK_a$ of ≥0.9, in particular free carboxylic acids, according to the invention.

Measurements

The analyses of metabolites, minerals, and enzymes were performed using the automated analyzers cobas 6000 C and 6000 E. Haemostasis tests and haematologic parameters were measured by STA-R (Diagnostica Stago) analyzer and LH 780 analyzer (Beckman Coulter) respectively. For results and comparative results see Examples 1-28.

ABBREVIATIONS

WBC: white blood cells; RBC: red blood cells; Hb: hemoglobin; Plt: platelets; Lympho: lymphocytes; Neutro: neutrophils; Mono: monocytes; Eos: eosinophils; Baso: basophils.

Alb: albumin; ALP: alkaline phosphatase; AST: aspartate aminotransferase; ALT: alanine aminotransferase; APTT: activated partial thromboplastin time; Ca: calcium; Chol: cholesterol; CREA: creatinine; CRP: C-reactive protein; Fe: iron; Fer: ferritin; Fib: fibrinogen; $FT_3$: triiodothyronine, free; $FT_4$: thyroxine, free; GGT: γ-glutamyltransferase; Gluc: glucose; K: potassium; Mg: magnesium; Na: sodium; PT: prothrombin time; TG: triglycerides; TP: total protein; TSH: thyrotropin.

Example 1

Example 1 shows a comparison between inventive sampling using citric acid monohydrate (in pristine blood collection KABEVETTE tubes (GR 15)) and conventional sampling using citrate (in Becton Dickinson tubes (BD)) for the determination of activated partial thromboplastin time (APTT) and prothrombin time (PT).

Example 2

Example 2 shows a comparison between inventive sampling using citric acid monohydrate (in pristine blood collection KABEVETTE tubes (GR 15)) and conventional sampling using $K_3$EDTA (in Becton Dickinson tubes (BD)) for the determination of white blood cells (WBC).

Example 3

Example 3 shows a comparison between inventive sampling using citric acid monohydrate (in pristine blood collection KABEVETTE tubes (GR 15)) and conventional sampling using $K_3$EDTA (in Becton Dickinson tubes (BD)) for the determination of lymphocytes (LYMPHO).

Example 4

Example 4 shows a comparison between inventive sampling using citric acid monohydrate (in pristine blood collection KABEVETTE tubes (GR 15)) and conventional sampling using $K_3$EDTA (in Becton Dickinson tubes (BD)) for the determination of basophils (Baso Etude) and monocytes (MONO).

Example 5

Example 5 shows a comparison between inventive sampling using citric acid monohydrate (in pristine blood collection KABEVETTE tubes (GR 15)) and conventional sampling using $K_3$EDTA (in Becton Dickinson tubes (BD)) for the determination of eosinophils (EOS).

Example 6

Example 6 shows a comparison between inventive sampling using citric acid monohydrate (in pristine blood collection KABEVETTE tubes (GR 15)) and conventional sampling using $K_3$EDTA (in Becton Dickinson tubes (BD)) for the determination of neutrophils (NEUTRO).

Example 7

Example 7 shows a comparison between inventive sampling using citric acid monohydrate (in pristine blood collection KABEVETTE tubes (GR 15)) and conventional sampling using $K_3$EDTA (in Becton Dickinson tubes (BD)) for the determination of haemoglobin (Hb).

Example 8

Example 8 shows a comparison between inventive sampling using citric acid monohydrate (in pristine blood collection KABEVETTE tubes (GR 15)) and conventional sampling using $K_3$EDTA (in Becton Dickinson tubes (BD)) for the determination of red blood cells (RBC).

Example 9

Example 9 shows a comparison between inventive sampling using citric acid monohydrate (in pristine blood collection KABEVETTE tubes (GR 15)) and conventional sampling using citrate (in Becton Dickinson tubes) for the determination of fibrinogen (FIB ETUDE) and a comparison between inventive sampling using citric acid monohydrate (in pristine blood collection KABEVETTE tubes (GR 15)) and conventional sampling using $K_3$EDTA (in Becton Dickinson tubes (BD)) for the determination of platelets (Ptl).

Example 10

Example 10 shows a comparison between inventive sampling using citric acid monohydrate (in pristine blood collection KABEVETTE tubes (GR 15)) and sampling using conventional serum samples (SST (BD)) for the determination of cholesterol (CHOL).

Example 11

Example 11 shows a comparison between inventive sampling using citric acid monohydrate (in pristine blood collection KABEVETTE tubes (GR 15)) and sampling using conventional serum samples (SST (BD)) for the determination of creatinine (CREA).

Example 12

Example 12 shows a comparison between inventive sampling using citric acid monohydrate (in pristine blood collection KABEVETTE tubes (GR 15)) and sampling using conventional serum samples (SST (BD)) for the determination of iron (Fe).

Example 13

Example 13 shows a comparison between inventive sampling using citric acid monohydrate (in pristine blood collection KABEVETTE tubes (GR 15)) and sampling using conventional serum samples (SST (BD)) for the determination of ferritin (Fer).

Example 14

Example 14 shows a comparison between inventive sampling using citric acid monohydrate (in pristine blood collection KABEVETTE tubes (GR 15)) and sampling using conventional serum samples (SST (BD)) for the determination of triiodothyronine, free (FT3).

Example 15

Example 15 shows a comparison between inventive sampling using citric acid monohydrate (in pristine blood collection KABEVETTE tubes (GR 15)) and sampling using conventional serum samples (SST (BD)) for the determination of glucose (Gluc).

Example 16

Example 16 shows a comparison between inventive sampling using citric acid monohydrate (in pristine blood collection KABEVETTE tubes (GR 15)) and sampling using conventional serum samples (SST (BD)) for the determination of aspartate aminotransferase (AST).

Example 17

Example 17 shows a comparison between inventive sampling using citric acid monohydrate (in pristine blood collection KABEVETTE tubes (GR 15)) and sampling using conventional serum samples (SST (BD)) for the determination of alanine aminotransferase (ALT).

Example 18

Example 18 shows a comparison between inventive sampling using citric acid monohydrate (in pristine blood collection KABEVETTE tubes (GR 15)) and conventional sampling using BD tubes for the determination of magnesium (Mg ETUDE) and calcium (Ca ETUDE).

Example 19

Example 19 shows a comparison between inventive sampling using citric acid monohydrate (in pristine blood collection KABEVETTE tubes (GR 15)) and sampling using conventional serum samples (SST (BD)) for the determination of alkaline phosphatase (ALP).

Example 20

Example 20 shows a comparison between inventive sampling using citric acid monohydrate (in pristine blood collection KABEVETTE tubes (GR 15)) and sampling using conventional serum samples (SST (BD)) for the determination of triglycerides (TG).

Example 21

Example 21 shows a comparison between inventive sampling using citric acid monohydrate (in pristine blood collection KABEVETTE tubes (GR 15)) and conventional sampling using BD tubes for the determination of thyrotropin (TSH) and thyroxine, free (FT4 ETUDE).

Example 22

Example 22 shows a comparison between inventive sampling using citric acid monohydrate (in pristine blood collection KABEVETTE tubes (GR 15)) and conventional sampling using BD tubes for the determination of C-reactive protein (CRP ETUDE).

Example 23

Example 23 shows a comparison between inventive sampling using citric acid monohydrate (in pristine blood collection KABEVETTE tubes (GR 15)) and conventional sampling using BD tubes for the determination of γ-glutamyltransferase (GGT ETUDE).

Example 24

Example 24 shows a comparison between inventive sampling using citric acid monohydrate (in pristine blood collection KABEVETTE tubes (GR 15)) and conventional sampling using BD tubes for the determination of potassium (K ETUDE).

Example 25

Example 25 shows a comparison between inventive sampling using citric acid monohydrate (in pristine blood collection KABEVETTE tubes (GR 15)) and conventional sampling using BD tubes for the determination of sodium (Na ETUDE).

Example 26

Example 26 shows a comparison between inventive sampling using citric acid monohydrate (in pristine blood collection KABEVETTE tubes (GR 15)) and conventional sampling using BD tubes for the determination of albumin (Alb ETUDE).

Example 27

Example 27 shows a comparison between inventive sampling using citric acid monohydrate (in pristine blood collection KABEVETTE tubes (GR 15)) and sampling using conventional serum samples (SST (BD)) for the determination of total protein (TP).

The results and concentrations of the respective parameters as determined in the inventive and reference samples in Examples 1 to 27 are shown below. The results of the inventive samples are completely statistically and medically comparable with results and concentrations obtained by using conventional sampling.

Method comparison: APTT
Methods: <APTT GR 15> versus <APTT citrate (BD)>

| Concentrations | Medical tolerance | Max non-equivalence error |
|---|---|---|
| <31.92 sec | 1.93 sec | 0.64 sec |
| 31.92 to 50.18 sec | 1.93 sec | 0.64 sec |
| >50.18 sec | 3.62 sec | 1.19 sec |

Distribution of concentrations:

| Method | Mean | SD | Min | Max | Unit | N |
|---|---|---|---|---|---|---|
| APTT citrate (BD) | 29.71 | 3.111 | 25.4 | 39.1 | sec | 48 |
| APTT GR 15 | 29.94 | 3.873 | 23.4 | 40.9 | | |

Method comparison: PT
Methods: <PT GR 15> versus <PT citrate (BD)>

| Concentrations | Medical tolerance | Max non-equivalence error |
|---|---|---|
| <38.17% | 4.48% | 1.48% |
| 38.17 to 88.50% | 6.67% | 2.20% |
| >88.50% | 8.85% | 2.92% |

Distribution of concentrations:

| Method | Mean | SD | Min | Max | Unit | N |
|---|---|---|---|---|---|---|
| TP Citrate | 95.1 | 13.91 | 29 | 100 | % | 50 |
| TP GR 15 | 89.3 | 13.72 | 32 | 100 | | |

Method comparison: WBC
Methods: <WBC GR 15> versus <WBC K3EDTA>

| Concentrations | Medical tolerance | Max non-equivalence error |
|---|---|---|
| <3.60/mm3 | 0.44/mm3 | 0.14/mm3 |
| 3.60 to 20.70/mm3 | 0.48/mm3 | 0.16/mm3 |
| >20.70/mm3 | 0.68/mm3 | 0.22/mm3 |

Distribution of concentrations:

| Method | Mean | SD | Min | Max | Unit | N |
|---|---|---|---|---|---|---|
| WBC K3EDTA | 9.44 | 15.68 | 3.8 | 117.7 | /mm3 | 51 |
| WBC GR 15 | 9.50 | 15.51 | 3.7 | 116.5 | | |

Method comparison: LYMPHO
Methods: <LYMPHO GR 15> versus <LYMPHO K3EDTA (BD)>

| Concentrations | Medical tolerance | Max non-equivalence error |
|---|---|---|
| <14.70% | 2.09% | 0.69% |
| 14.70 to 47.80% | 2.09% | 0.69% |
| >47.80% | 2.59% | 0.85% |

Distribution of concentrations:

| Method | Mean | SD | Min | Max | Unit | N |
|---|---|---|---|---|---|---|
| LYMPHO K3EDTA (BD) | 32.000 | 12.29 | 7.10 | 88.50 | % | 48 |
| LYMPHO GR 15 | 32.05 | 11.65 | 7.6 | 80.6 | | |

Method comparison: Baso Etude
Methods: <Tube GR 15> versus <Tube EDTA>

| Concentrations | Medical tolerance | Max non-equivalence error |
|---|---|---|
| <0.10% | 0.22% | 0.07% |
| 0.10 to 0.20% | 0.22% | 0.07% |
| >0.20% | 0.38% | 0.12% |

Distribution of concentrations:

| Method | Mean | SD | Min | Max | Unit | N |
|---|---|---|---|---|---|---|
| Tube EDTA | 0.48 | 0.1869 | 0.0 | 1.0 | % | 50 |
| Tube GR 15 | 0.47 | 0.1708 | 0.1 | 0.9 | | |

Method comparison: MONO
Methods: <MONO GR 15> versus <MONO K3EDTA (BD)>

| Concentrations | Medical tolerance | Max non-equivalence error |
|---|---|---|
| <5.60% | 0.99% | 0.33% |
| 5.60 to 15.10% | 1.89% | 0.62% |
| >15.10% | 2.31% | 0.76% |

Distribution of concentrations:

| Method | Mean | SD | Min | Max | Unit | N |
|---|---|---|---|---|---|---|
| MONO K3EDTA (BD) | 7.80 | 2.245 | 3.9 | 13.5 | % | 48 |
| MONO GR 15 | 7.85 | 2.081 | 3.8 | 13.7 | | |

Method comparison: EOS
Methods: <EOS GR 15> versus <EOS K3EDTA (BD)>

| Concentrations | Medical tolerance | Max non-equivalence error |
|---|---|---|
| <4.30% | 1.34% | 0.44% |
| 4.30 to 7.50% | 1.48% | 0.49% |
| >7.50% | 1.82% | 0.60% |

Distribution of concentrations:

| Method | Mean | SD | Min | Max | Unit | N |
|---|---|---|---|---|---|---|
| EOS K3EDTA (BD) | 2.97 | 2.341 | 0.1 | 12.6 | % | 48 |
| EOS GR 15 | 3.01 | 2.279 | 0.0 | 12.2 | | |

Method comparison: NEUTRO
Methods: <NEUTRO GR 15> versus <NEUTRO K3EDTA (BD)>

| Concentrations | Medical tolerance | Max non-equivalence error |
|---|---|---|
| <42.10% | 2.43% | 0.80% |
| 42.10 to 64.70% | 2.90% | 0.96% |
| >64.70% | 3.54% | 1.17% |

Distribution of concentrations:

| Method | Mean | SD | Min | Max | Unit | N |
|---|---|---|---|---|---|---|
| NEUTRO K3EDTA (BD) | 56.94 | 13.37 | 4.3 | 81.9 | % | 49 |
| NEUTRO GR 15 | 56.68 | 13.21 | 4.0 | 81.8 | | |

Method comparison: Hb
Methods: <Hb GR 15> versus <Hb K3EDTA (BD)>

| Concentrations | Medical tolerance | Max non-equivalence error |
|---|---|---|
| <5.1 g/l | 0.2 g/l | 0.1 g/l |
| 5.1 to 16.1 g/l | 0.3 g/l | 0.1 g/l |
| >16.1 g/l | 0.3 g/l | 0.1 g/l |

Distribution of concentrations:

| Method | Mean | SD | Min | Max | Unit | N |
|---|---|---|---|---|---|---|

Method comparison: Hb
Methods: <Hb GR 15> versus <Hb K3EDTA (BD)>

| | | | | | | |
|---|---|---|---|---|---|---|
| Hb K3EDTA (BD) | 14.88 | 1.231 | 12.1 | 17.5 | g/l | 48 |
| Hb GR 15 | 14.42 | 1.237 | 11.5 | 17.0 | | |

Method comparison: RBC
Methods: <RBC GR 15> versus <RBC K3EDTA (BD)>

| Concentrations | Medical tolerance | Max non-equivalence error |
|---|---|---|
| <1.87/mm3 | 0.05/mm3 | 0.02/mm3 |
| 1.87 to 5.32/mm3 | 0.12/mm3 | 0.04/mm3 |
| >5.32/mm3 | 0.13/mm3 | 0.04/mm3 |

Distribution of concentrations:

| Method | Mean | SD | Min | Max | Unit | N |
|---|---|---|---|---|---|---|
| RBC K3EDTA (BD) | 4.732 | 0.5232 | 3.56 | 6.36 | /mm3 | 47 |
| RBC GR 15 | 4.580 | 0.5223 | 3.45 | 6.18 | | |

Method comparison: FIB ETUDE
Methods: <FIB GR 15> versus <FIB tube citrate>

| Concentrations | Medical tolerance | Max non-equivalence error |
|---|---|---|
| <1.13 g/l | 0.11 g/l | 0.04 g/l |
| 1.13 to 2.44 g/l | 0.11 g/l | 0.04 g/l |
| >2.44 g/l | 0.25 g/l | 0.08 g/l |

Distribution of concentrations:

| Method | Mean | SD | Min | Max | Unit | N |
|---|---|---|---|---|---|---|
| FIB tube citrate | 3.707 | 1.161 | 1.54 | 8.25 | g/l | 50 |
| FIB GR 15 | 4.445 | 1.344 | 2.06 | 9.75 | | |

Method comparison: Ptl
Methods: <Ptl GR 15> versus <Ptl K3EDTA (BD)>

| Concentrations | Medical tolerance | Max non-equivalence error |
|---|---|---|
| <69.00/mm3 | 8.13/mm3 | 2.68/mm3 |
| 69.00 to 429.00/mm3 | 19.16/mm3 | 6.32/mm3 |
| >429.00/mm3 | 33.75/mm3 | 11.14/mm3 |

Distribution of concentrations:

| Method | Mean | SD | Min | Max | Unit | N |
|---|---|---|---|---|---|---|
| Ptl K3EDTA (BD) | 238.0 | 55.41 | 127 | 352 | /mm3 | 46 |
| Ptl GR 15 | 233.4 | 56.65 | 124 | 358 | | |

Method comparison: CHOL
Methods: <CHOL GR 15> versus <CHOL SST (BD)>

| Concentrations | Medical tolerance | Max non-equivalence error |
|---|---|---|
| <1.16 g/l | 0.20 g/l | 0.07 g/l |
| 1.16 to 3.10 g/l | 0.33 g/l | 0.11 g/l |
| >3.10 g/l | 0.53 g/l | 0.17 g/l |

Distribution of concentrations:

| Method | Mean | SD | Min | Max | Unit | N |
|---|---|---|---|---|---|---|
| CHOL SST (BD) | 2.106 | 0.3692 | 1.36 | 2.86 | g/l | 45 |
| CHOL GR 15 | 2.154 | 0.379 | 1.39 | 3.02 | | |

Method comparison: CREA
Methods: <CREA GR 15> versus <CREA SST (BD)>

| Concentrations | Medical tolerance | Max non-equivalence error |
|---|---|---|
| <5.65 mg/l | 1.47 mg/l | 0.48 mg/l |
| 5.65 to 66.67 mg/l | 3.05 mg/l | 1.01 mg/l |
| >66.67 mg/l | 6.78 mg/l | 2.24 mg/l |

Distribution of concentrations:

| Method | Mean | SD | Min | Max | Unit | N |
|---|---|---|---|---|---|---|
| CREA SST(BD) | 10.07 | 5.175 | 5.8 | 40.7 | mg/l | 45 |
| CREA GR 15 | 10.29 | 4.92 | 5.9 | 39.0 | | |

Method comparison: Fe
Methods: <Fe GR 15> versus <Fe SST (BD)>

| Concentrations | Medical tolerance | Max non-equivalence error |
|---|---|---|
| <27.93 µg/dl | 9.50 µg/dl | 3.13 µg/dl |
| 27.93 to 223.46 µg/dl | 23.46 µg/dl | 7.74 µg/dl |
| >223.46 µg/dl | 37.99 µg/dl | 12.54 µg/dl |

Distribution of concentrations:

| Method | Mean | SD | Min | Max | Unit | N |
|---|---|---|---|---|---|---|
| Fe SST (BD) | 108.18 | 36.47 | 20.5 | 208.4 | µg/dl | 45 |
| Fe GR 15 | 110.80 | 37.44 | 18.7 | 217.6 | | |

Method comparison: Fer Ferritin
Methods: <Fer GR 15> versus <Fer SST (BD)>

| Concentrations | Medical tolerance | Max non-equivalence error |
|---|---|---|
| <20.00 ng/ml | 8.50 ng/ml | 2.81 ng/ml |
| 20.00 to 800.00 ng/ml | 68.00 ng/ml | 22.44 ng/ml |
| >800.00 ng/ml | 272.00 ng/ml | 89.76 ng/ml |

Distribution of concentrations:

| Method | Mean | SD | Min | Max | Unit | N |
|---|---|---|---|---|---|---|
| Fer SST (BD) | 248.854 | 205.5 | 1.12 | 815.00 | ng/ml | 45 |
| Fer GR 15 | 254.266 | 214.1 | 1.19 | 840.10 | | |

Method comparison: FT3
Methods: <Glu GR 15> versus <Glu SST BD>

| Concentrations | Medical tolerance | Max non-equivalence error |
|---|---|---|
| <1.95 ng/l | 0.91 ng/l | 0.30 ng/l |
| 1.95 to 9.77 ng/l | 1.56 ng/l | 0.52 ng/l |
| >9.77 ng/l | 3.32 ng/l | 1.10 ng/l |

Distribution of concentrations:

| Method | Mean | SD | Min | Max | Unit | N |
|---|---|---|---|---|---|---|
| FT3 SST(BD) | 3.115 | 0.4417 | 2.12 | 4.17 | ng/l | 45 |
| FT3 GR 15 | 3.159 | 0.4371 | 2.29 | 4.24 | | |

Method comparison: Gluc
Methods: <Glu GR 15> versus <Glu SST BD>

| Concentrations | Medical tolerance | Max non-equivalence error |
|---|---|---|
| <0.36 g/l | 0.05 g/l | 0.02 g/l |
| 0.36 to 2.88 g/l | 0.11 g/l | 0.04 g/l |
| >2.88 g/l | 0.20 g/l | 0.07 g/l |

Distribution of concentrations:

| Method | Mean | SD | Min | Max | Unit | N |
|---|---|---|---|---|---|---|
| Glu SST BD | 1.076 | 0.3619 | 0.78 | 2.90 | g/l | 44 |
| Glu GR 15 | 1.074 | 0.3427 | 0.78 | 2.79 | | |

Method comparison: AST
Methods: <AST GR 15> versus <AST SST (BD)>

| Concentrations | Medical tolerance | Max non-equivalence error |
|---|---|---|
| <20.00 UI/l | 5.00 UI/l | 1.65 UI/l |
| 20.00 to 200.00 UI/l | 13.00 UI/l | 4.29 UI/l |
| >200.00 UI/l | 42.00 UI/l | 13.86 UI/l |

Distribution of concentrations:

| Method | Mean | SD | Min | Max | Unit | N |
|---|---|---|---|---|---|---|
| AST SST (BD) | 26.7 | 14.09 | 14 | 94 | UI/l | 44 |
| AST GR 15 | 26.4 | 14.1 | 13 | 94 | | |

Method comparison: ALT
Methods: <ALT GR 15> versus <ALT SST (BD)>

| Concentrations | Medical tolerance | Max non-equivalence error |
|---|---|---|
| <20.00 UI/l | 5.00 UI/l | 1.65 UI/l |
| 20.00 to 200.00 UI/l | 13.00 UI/l | 4.29 UI/l |
| >200.00 UI/l | 42.00 UI/l | 13.86 UI/l |

Distribution at concentrations:

| Method | Mean | SD | Min | Max | Unit | N |
|---|---|---|---|---|---|---|
| ALT SST (BD) | 30.2 | 20.24 | 8 | 115 | UI/l | 45 |
| ALT GR 15 | 30.1 | 20.22 | 10 | 116 | | |

Method comparison: Mg ETUDE
Method: <TUBE GR15> versus <TUBE BD>

| Concentrations | Medical tolerance | Max non-equivalence error |
|---|---|---|
| <12.1 mg/l | 1.9 mg/l | 0.6 mg/l |
| 12.1 to 38.8 mg/l | 2.9 mg/l | 1.0 mg/l |
| >38.8 mg/l | 5.3 mg/l | 1.8 mg/l |

Distribution of concentractions:

| Method | Mean | SD | Min | Max | Unit | N |
|---|---|---|---|---|---|---|
| TUBE BD | 22.07 | 7.905 | 16.0 | 55.0 | mg/l | 44 |
| TUBE GR15 | 22.10 | 7.662 | 15.9 | 52.0 | | |

Method comparison: Ca ETUDE
Methods: <TUBE GR15> versus <TUBE BD>

| Concentrations | Medical tolerance | Max non-equivalence error |
|---|---|---|
| <72.00 mg/l | 4.80 mg/l | 1.58 mg/l |
| 72.00 to 136.00 mg/l | 6.40 mg/l | 2.11 mg/l |
| >136.00 mg/l | 9.20 mg/l | 3.04 mg/l |

Distribution of concentrations:

| Method | Mean | SD | Min | Max | Unit | N |
|---|---|---|---|---|---|---|
| TUBE BD | 93.44 | 4.272 | 80.7 | 110.0 | mg/l | 45 |
| TUBE GR15 | 104.69 | 4.211 | 92.3 | 112.9 | | |

Method comparison: ALP
Methods: <ALP GR 15> versus <ALP SST (BD)>

| Concentrations | Medical tolerance | Max non-equivalence error |
|---|---|---|
| <20.0 U/L | 5.0 U/L | 1.7 U/L |
| 20.0 to 390.0 U/L | 12.0 U/L | 4.0 U/L |
| >390.0 U/L | 83.0 U/L | 27.4 U/L |

Distribution of concentrations:

| Method | Mean | SD | Min | Max | Unit | N |
|---|---|---|---|---|---|---|
| ALP SST (BD) | 74.1 | 28.99 | 26 | 221 | U/L | 45 |
| ALP GR 15 | 66.0 | 25.82 | 21 | 195 | | |

Method comparison: TG
Methods: <TG GR 15> versus <TG SST (BD)>

| Concentrations | Medical tolerance | Max non-equivalence error |
|---|---|---|
| <0.44 g/L | 0.11 g/L | 0.03 g/L |
| 0.44 to 2.65 g/L | 0.27 g/L | 0.09 g/L |
| >2.65 g/L | 0.54 g/L | 0.18 g/L |

Distribution of concentrations:

| Method | Mean | SD | Min | Max | Unit | N |
|---|---|---|---|---|---|---|
| TG SST (BD) | 1.693 | 1.096 | 0.68 | 5.85 | g/L | 45 |
| TG GR 15 | 1.726 | 1.121 | 0.69 | 5.94 | | |

Method comparison: TSH
Methods: <TSH GR 15> versus <TSH SST (BD)>

| Concentrations | Medical tolerance | Max non-equivalence error |
|---|---|---|
| <0.10 mUI/l | 0.10 mUI/l | 0.03 mUI/l |
| 0.10 to 30.00 mUI/l | 0.30 mUI/l | 0.10 mUI/l |
| >30.00 mUI/l | 6.40 mUI/l | 2.11 mUI/l |

Distribution of concentrations:

| Method | Mean | SD | Min | Max | Unit | N |
|---|---|---|---|---|---|---|
| TSH SST (BD) | 2.3579 | 1.618 | 0.661 | 8.160 | mUI/l | 45 |
| TSH GR 15 | 2.4635 | 1.72 | 0.715 | 9.100 | | |

Method comparison: FT4 ETUDE
Methods: <TUBE GR15> versus <TUBE BD>

| Concentrations | Medical tolerance | Max non-equivalence error |
|---|---|---|
| <7.77 pg/ml | 3.26 pg/ml | 1.08 pg/ml |
| 7.77 to 19.43 pg/ml | 4.51 pg/ml | 1.49 pg/ml |
| >19.43 pg/ml | 6.61 pg/ml | 2.18 pg/ml |

Distribution of concentrations:

| Method | Mean | SD | Min | Max | Unit | N |
|---|---|---|---|---|---|---|

-continued

| | | | | | |
|---|---|---|---|---|---|
| TUBE BD | 12.691 | 1.865 | 8.78 | 18.63 | pg/ml | 45 |
| TUBE GR15 | 13.119 | 1.878 | 9.08 | 18.77 | | |

Method comparison: CRP ETUDE
Methods: <TUBE GR15> versus <TUBE BD>

| Concentrations | Medical tolerance | Max non-equivalence error |
|---|---|---|
| <15.00 mg/l | 7.60 mg/l | 2.51 mg/l |
| 15.00 to 100.00 mg/l | 12.70 mg/l | 4.19 mg/l |
| >100.00 mg/l | 21.20 mg/l | 7.00 mg/l |

Distribution of concentrations:

| Method | Mean | SD | Min | Max | Unit | N |
|---|---|---|---|---|---|---|
| TUBE BD | 8.26 | 26.47 | 0.1 | 168.0 | mg/l | 45 |
| TUBE GR15 | 7.94 | 25.04 | 0.0 | 158.1 | | |

Method comparison: GGT ETUDE
Methods: <TUBE GR15> versus <TUBE BD>

| Concentrations | Medical tolerance | Max non-equivalence error |
|---|---|---|
| <20.00 UI/l | 5.00 UI/l | 1.65 UI/l |
| 20.00 to 390.00 UI/l | 13.00 UI/l | 4.29 UI/l |
| >390.00 UI/l | 83.00 UI/l | 27.39 UI/l |

Distribution of concentrations:

| Method | Mean | SD | Min | Max | Unit | N |
|---|---|---|---|---|---|---|
| TUBE BD | 57.6 | 155.2 | 6 | 1055 | UI/l | 45 |
| TUBE GR15 | 58.7 | 160 | 6 | 1088 | | |

Method comparison: K ETUDE
Methods: <Tube GR15> versus <Tube BD>

| Concentrations | Medical tolerance |
|---|---|
| <2.00 mmol/l | 0.17 mmol/l |
| 2.00 to 6.00 mmol/l | 0.27 mmol/l |
| >6.00 mmol/l | 0.41 mmol/l |

Distribution of concentrations:

| Method | Mean | SD | Min | Max | Unit | N |
|---|---|---|---|---|---|---|
| TUBE BD | 4.61 | 0.4717 | 3.5 | 5.6 | mmol/l | 45 |
| TUBE GR15 | 4.73 | 0.4611 | 3.5 | 5.8 | | |

Method comparison: Na ETUDE
Methods: <Tube GR15> versus <Tube BD>

| Concentrations | Medical tolerance | Max non-equivalence error |
|---|---|---|
| <120.00 mmol/l | 6.60 mmol/l | 2.18 mmol/l |
| 120.00 to 160.00 mmol/l | 6.50 mmol/l | 2.15 mmol/l |
| >160.00 mmol/l | 6.10 mmol/l | 2.01 mmol/l |

Method comparison: Na ETUDE
Methods: <Tube GR15> versus <Tube BD>

Distribution of concentrations:

| Method | Mean | SD | Min | Max | Unit | N |
|---|---|---|---|---|---|---|
| Tube BD | 142.0 | 2.121 | 138 | 149 | mmol/l | 45 |
| Tube GR15 | 146.3 | 2.31 | 142 | 151 | | |

Method comparison: Alb ETUDE
Methods: <TUBE GR15> versus <TUBE BD>

| Concentrations | Medical tolerance | Max non-equivalence error |
|---|---|---|
| <20.0 g/l | 5.1 g/l | 1.7 g/l |
| 20.0 to 50.0 g/l | 6.4 g/l | 2.1 g/l |
| >50.0 g/l | 8.5 g/l | 2.8 g/l |

Distribution of concentrations:

| Method | Mean | SD | Min | Max | Unit | N |
|---|---|---|---|---|---|---|
| TUBE BD | 46.58 | 2.871 | 40.9 | 53.0 | g/l | 45 |
| TUBE GR15 | 48.53 | 2.71 | 42.4 | 55.4 | | |

Method comparison: TP
Methods: <TP GR 15> versus <TP SST BD>

| Concentrations | Medical tolerance | Max non-equivalence error |
|---|---|---|
| <40.0 g/l | 5.4 g/l | 1.8 g/l |
| 40.0 to 90.0 g/l | 6.6 g/l | 2.2 g/l |
| >90.0 g/l | 9.2 g/l | 3.0 g/l |

Distribution of concenrations:

| Method | Mean | SD | Min | Max | Unit | N |
|---|---|---|---|---|---|---|
| TP SST BD | 70.7 | 3.219 | 65 | 80 | g/l | 41 |
| TP GR 15 | 76.1 | 3.58 | 70 | 85 | | |

Example 28

Full blood cell counts and white blood cell differential analysis were performed for samples from blood collection tubes according to the present invention using as anticoagulant respectively CA, TCA, EDTA, DTPA, MELA, THTCA, and BPCA. For a comparison, results are shown for samples with potassium EDTA ($K_3EDTA(BD)$). The results for the inventive samples are completely statistically and medically comparable with those obtained with conventional $K_3EDTA$ as anticoagulant (see Table 1), showing that anticoagulants according to the present invention effectively inhibit coagulation.

TABLE 1

|  | K3EDTA (BD) | CA | TCA | EDTA | DTPA | MELA | THTCA | BPCA |
|---|---|---|---|---|---|---|---|---|
| WBC ($10^3/\mu l$) | 6.56 | 6.54 | 6.6 | 6.23 | 6.53 | 6.3 | 6.42 | 5.9 |
| RBC ($10^6/\mu l$) | 4.58 | 4.53 | 4.49 | 4.44 | 4.52 | 4.53 | 4.49 | 4.55 |
| Hb (g/dL) | 14.3 | 14.2 | 14.2 | 13.8 | 14.1 | 14.2 | 14.2 | 14.2 |
| HCT (%) | 42.2 | 42.0 | 43.4 | 41.9 | 42.3 | 42.8 | 43.1 | 46.1 |
| MCV (fl) | 92.1 | 93.0 | 96.7 | 94.4 | 93.6 | 94.5 | 96.0 | 101 |
| MCH (pg) | 31.2 | 31.3 | 31.6 | 31.1 | 31.2 | 31.3 | 31.6 | 31.2 |
| MCHC (g/dL) | 33.9 | 33.8 | 32.7 | 32.9 | 33.3 | 33.2 | 32.9 | 30.8 |
| PLT ($10^3/\mu l$) | 283 | 270 | 287 | 266 | 210 | 270 | 255 | 250 |
| NEUTRO (%) | 68.4 | 68.5 | 69.0 | 70.8 | 70.3 | 68.3 | 68.6 | 68.9 |
| LYMPHO (%) | 22.0 | 22.0 | 22.0 | 19.9 | 20.5 | 22.4 | 22.3 | 21.7 |
| MONO (%) | 7.6 | 8.0 | 7.6 | 7.9 | 7.7 | 7.8 | 7.6 | 7.5 |
| EOS (%) | 0.9 | 0.7 | 0.7 | 0.6 | 0.8 | 0.8 | 0.8 | 0.7 |
| BASO | 1.1 | 0.8 | 0.7 | 0.8 | 0.8 | 0.7 | 0.8 | 1.2 | n = 10

Abbreviations:
HCT: hematocrit,
MCV: mean corpuscular volume,
MCH: mean corpuscular hemoglobin,
MCHC: mean corpuscular hemoglobin concentration Example 29

Tests were carried out to determine haemoglobin (Hb).

Example 29A shows a comparison between sampling using citric acid monohydrate (in pristine blood collection KABEVETTE tubes (GR15)) and conventional sampling using K₃EDTA (in Becton Dickinson tubes (BD)) for the determination of haemoglobin (Hb). The citric acid solution contained no alkylammonium compound and the pH 1.8 was not adjusted. See FIG. 1 for results.

Example 29B shows a comparison between sampling using citric acid monohydrate (in pristine blood collection KABEVETTE tubes (HCT)) and conventional sampling using K₃EDTA (in Becton Dickinson tubes (BD)) for the determination of haemoglobin (Hb). The citric acid solution contained alkylammonium salt, in particular tetramethylammonium chloride in a concentration of 16 μmol/ml of blood, and the pH was adjusted to 2.4. See FIG. 1 for results.

Example 30

Tests were carried out to determine chloride ions (Cl).

Example 30A shows a comparison between sampling using citric acid monohydrate (in pristine blood collection KABEVETTE tubes (GR15)) and conventional sampling using K₃EDTA (in Becton Dickinson tubes (BD)) for the determination of chloride ions (Cl). The citric acid solution contained no alkylammonium compound and the pH 1.8 was not adjusted. See FIG. 2 for results.

Example 30B shows a comparison between sampling using citric acid monohydrate (in pristine blood collection KABEVETTE tubes (HCT)) and conventional sampling using K₃EDTA (in Becton Dickinson tubes (BD)) for the determination of chloride ions (Cl). The citric acid solution contained alkylammonium salt, in particular tetramethylammonium chloride in a concentration of 16 μmol/ml of blood, and the pH was adjusted to 2.4. See FIG. 2 for results.

The invention claimed is:

1. A method for collecting and analyzing and optionally storing blood in vitro, comprising:
    providing a blood collection device,
    mixing blood after its withdrawal in said blood collection device with citric acid as the only anticoagulant, wherein said citric acid is provided as a free acid having a pKa of >0.9, wherein the concentration of said citric acid provided as free acid having a pKa of >0.9 is at least 0.1 mmol/L of blood mixed therewith, wherein the citric acid comprises three carboxyl groups per molecule,
    wherein said mixing is carried out under conditions that in the citric acid as provided, all of the carboxyl groups in the molecule are protonated,
    wherein coagulation in blood is thereby inhibited,
    wherein the blood, collected in a single device and mixed with citric acid and optionally after being stored in the blood collection device for a desired period of time, is subsequently subjected to at least one test for the determination of at least one blood component, and further to multiple tests comprising at least one hematologic test, at least one coagulation test and at least one further clinical chemistry analysis.

2. The method according to claim 1, wherein said citric acid is:
    (i) provided as free acid having a pKa of >0.9; or
    (ii) provided as free acid having a pKa of >0.9 dissolved in a solvent.

3. The method according to claim 2, wherein in case (ii) the solvent is selected from the group consisting of an aqueous solution, water, and alcohol and mixtures of water and alcohol.

* * * * *